US006800302B2

(12) United States Patent
Cannell et al.

(10) Patent No.: US 6,800,302 B2
(45) Date of Patent: Oct. 5, 2004

(54) HEAT ACTIVATED DURABLE STYLING COMPOSITIONS COMPRISING $C_1$ TO $C_{22}$ SUBSTITUTED $C_3$-$C_5$ MONOSACCHARIDES AND METHODS FOR SAME

(75) Inventors: David W. Cannell, Plainfield, NJ (US); Nghi Van Nguyen, Edison, NJ (US)

(73) Assignee: L'Oreal S.A., Paris (FR)

( * ) Notice: Subject to any disclaimer, the term of this patent is extended or adjusted under 35 U.S.C. 154(b) by 0 days.

(21) Appl. No.: 09/820,856

(22) Filed: Mar. 30, 2001

(65) Prior Publication Data

US 2002/0182163 A1 Dec. 5, 2002

(51) Int. Cl.[7] .............................. A61K 7/09; A61K 7/11
(52) U.S. Cl. .................................... 424/702; 424/70.13
(58) Field of Search ............................. 424/70.2, 70.13, 424/70.1, 70.11, 70.15, 70.16, 70.17

(56) References Cited

U.S. PATENT DOCUMENTS

| | | | |
|---|---|---|---|
| 4,900,545 A | 2/1990 | Wisotzki et al. | |
| 4,971,080 A | 11/1990 | Rubenstein et al. | |
| 5,348,737 A | 9/1994 | Syed et al. | |
| 5,641,477 A | 6/1997 | Syed et al. | |
| 5,660,838 A | 8/1997 | Koga et al. | |
| 5,688,930 A | * 11/1997 | Bertho et al. | ............... 536/18.6 |
| 5,888,951 A | 3/1999 | Gagnebien et al. | |
| 6,235,298 B1 | * 5/2001 | Naser et al. | ................ 424/401 |
| 6,486,105 B1 | * 11/2002 | Cannell et al. | ............. 510/124 |
| 6,495,147 B1 | 12/2002 | Dumas et al. | |

FOREIGN PATENT DOCUMENTS

| | | |
|---|---|---|
| DE | 3820030 | 7/1989 |
| DE | 4413434 | 10/1995 |
| DE | 4440315 | 5/1996 |
| EP | 398177 | 11/1990 |
| EP | 469232 | 2/1992 |
| EP | 555086 | 12/1995 |
| EP | 750900 | 1/1997 |
| EP | 829255 | 3/1998 |
| FR | 2704751 | 11/1994 |
| JP | 01213213 | 8/1989 |
| JP | 02204407 | 8/1990 |
| JP | 04273806 | 2/1991 |
| JP | 03148211 | 6/1991 |
| JP | 03240730 | 10/1991 |
| JP | 04266812 | 9/1992 |
| JP | 05221823 | 8/1993 |
| JP | 06122614 | 5/1994 |
| JP | 06287110 | 10/1994 |
| JP | 07258041 | 10/1995 |
| JP | 09124453 | 11/1995 |
| JP | 08151313 | 6/1996 |
| JP | 08217656 | 8/1996 |
| JP | 10017430 | 1/1998 |
| JP | 10279439 | 10/1998 |
| JP | 10306017 | 11/1998 |
| WO | WO 9323512 | 11/1993 |
| WO | WO 01/18096 | 3/2001 |
| WO | WO 9924009 | 12/2002 |

OTHER PUBLICATIONS

Harry's Cosmeticology By Ralph Harry, pp 470–483 (1982).*
Milczarek et al., "The Mechanism and Stability of Thermal Transitions in Hair Keratin", *Colloid and Polymer Science*, vol. 270, No. 11, 1992, pp. 1106–1115.
Spei et al., "Thermoanalytical Investigations of Extended and Annealed Keratins", *Colloid & Polymer Science*, vol. 265, No. 11, 1987, pp. 965–970.
Sandhu et al., "A Simple and Sensitive Technique, Based on Protein Loss Measurements, to Assess Surface Damage to Human Hair", *J. Soc. Cosmet. Chem*, vol. 44, No. 3, May/Jun. 1993, pp. 163–175.
English language Derwent Abstract of DE 297 09 853, Sep. 20, 1994.
English language Derwent Abstract of JP 06–122614, May 6, 1994.
English language Derwent Abstract of JP 04–266812, Sep. 22, 1992.
English language Derwent Abstract of JP 10–279439, Oct. 20, 1998.
English language Derwent Abstract of JP 09–059134, Mar. 4, 1997.
English language ACS abstract 12–5:30893, Song et al., "Antimutagenic effect of vitamin B12 and glucose in cold waving agent (a hair conditioner)", *Gongye Weisheng Yu Zhiyebing*,1996, 22(1), pp. 12–13.
English language ACS abstract 123:296216, Hollenberg et al., "Possibilities of influencing hair structure with hair–care preparations", *SOFW J.*, 1995, 121(2), pp. 82–6, 88–9.
English language ACS abstract 114:149908, Hollenberg et al., "Possibilities of influencing hair structure with cosmetic formulations", *Seifen, Oele, Fette, Wachse*, 1991, 117(1), pp. 9–13.
English language ACS abstract 123:289411, Trezl et al., "Increase in dye pick–up of wool caused by the Maillard reaction", *J. Soc. Dyers Colour*, 1995, 111(9), pp. 293–297.
English language ACS abstract 109:56463, Forst et al., "Modification of wool fibers during chemical treatment applied for dyeing optimization", *Ind. Usoara: Text., Tricotaje, Confectii Text.*, 1987, 38(12), p. 560–2.
English language ACS abstract 79:141244, Fujiwara et al., "Amino–carbonyl reaction of wool", *Sen'l Gakkaishi*, 1972, 28(4–5), pp. 142–146.
CTFA International Cosmetic Ingredient Dictionary, 8th edition, pp. 1744 to 1747 (2000).

* cited by examiner

Primary Examiner—Jyothsna Venkat
(74) Attorney, Agent, or Firm—Finnegan, Henderson, Farabow, Garrett & Dunner, L.L.P.

(57) ABSTRACT

Compositions, optionally heat-activated, methods and kits for durable non-permanent shaping of at least one keratinous fiber or for durable retention of a non-permanent shape of at least one keratinous fiber comprising applying to keratinous fibers a composition comprising at least one compound chosen from $C_3$ to $C_5$ monosaccharides substituted with at least one $C_1$ to $C_{22}$ carbon chain, and heating the keratinous fibers.

112 Claims, No Drawings

HEAT ACTIVATED DURABLE STYLING COMPOSITIONS COMPRISING $C_1$ TO $C_{22}$ SUBSTITUTED $C_3$-$C_5$ MONOSACCHARIDES AND METHODS FOR SAME

The present invention relates to compositions, kits comprising these compositions, and methods for using these compositions for durable non-permanent shaping or for durable retention of a non-permanent shape of at least one keratinous fiber, including human keratinous fibers, by applying to the at least one keratinous fiber compositions which comprise at least one compound chosen from $C_3$ to $C_5$ monosaccharides substituted with at least one $C_1$ to $C_{22}$ carbon chain, and, in certain embodiments, at least one film forming agent different from the at least one compound, and heating the at least one keratinous fiber. These compositions may both impart a durable non-permanent shape to the at least one keratinous fiber and durably retain a non-permanent shape of the at least one keratinous fiber.

In today's market, many consumers prefer the flexibility of non-permanent hairstyles, that is, those styles obtained via non-permanent shaping of the hair. Typically, such non-permanent styles disappear when the hair is wetted, especially when the hair is washed with water and/or shampoo. Methods for non-permanent shaping of keratinous fibers include, for example, brushing, teasing, braiding, the use of hair rollers, and heat styling, optionally with a commercially available styling product. Non-limiting examples of heat styling include blow drying, crimping and curling methods using elevated temperatures (such as, for example, setting hair in curlers and heating, and curling with a curling iron and/or hot rollers).

While such compositions and methods may provide for non-permanent shaping of keratinous fibers, many consumers desire a higher degree of styling than most commercially available products and methods employing these products provide. For example, many consumers desire compositions and methods that improve non-permanent curl formation. There is a need, therefore, for compositions and methods for non-permanent shaping of keratinous fibers that result in a higher degree of styling, such as non-permanent curl formation.

Further, many people desire compositions and methods for retaining a particular non-permanent shape or style of keratinous fibers such as hair. A common way to retain a particular hairstyle is with the use of a hairspray, typically applied after styling the hair. Other methods to retain a hairstyle or shape of keratinous fibers include the use of mousses, gels, and lotions. The materials in these compositions are generally film forming agents, resins, gums, and/or adhesive polymers.

While such compositions and methods may provide for non-permanent shaping of keratinous fibers, many consumers desire compositions and methods for durable retention of a particular non-permanent shape or style of keratinous fibers such as hair, such as, for example, those that hold or maintain a shape of a keratinous fiber until the keratinous fiber is washed with water and/or shampoo. Further, many consumers desire compositions and methods that allow hair to retain a particular shape longer than untreated hair, even after washing or shampooing the hair.

Thus, while commercially available compositions may provide temporary setting benefits, many consumers desire a higher level of retention or hold. Good holding power is one attribute a consumer looks for in styling products for keratinous fibers. Specifically, curl retention under conditions of changing humidity, for example changes to a higher humidity, is sought after by the consumer. Further, good curl retention in damaged hair is important to the consumer since the hair fiber has been weakened and will be less likely to maintain the curl. Therefore, there is also a need for methods for durably retaining a shape of keratinous fibers even under conditions of high humidity, such as at atmospheric humidity above 40%.

Sugars and sugar derivatives are one class of the countless number of compounds that have been added to hair care compositions. Documented uses of sugars in hair care compositions include: the use of glucose to improve the tactile and elastic properties of natural hair (Hollenberg and Mueller, *SOFW J.* 121(2) (1995)); the use of glucose for hair damage prophylaxis and damaged hair repair (Hollenberg & Matzik, *Seifen, Oele, Fette, Wachase* 117(1) (1991)); the use of glucose in shampoos (J04266812, assigned to Lion Corp.); the use of trehalose for moisture retention (J06122614, assigned to Shiseido Co. Ltd.); a composition for the lanthionization of hair comprising a sugar (U.S. Pat. Nos. 5,348,737 and 5,641,477, assigned to Avlon Ind. Inc.); the incorporation of xylobiose into cosmetic compositions to provide enhanced moisture retention and reduce excessive roughness and dryness of the skin and hair (U.S. Pat. No. 5,660,838, assigned to Suntory Ltd.); a composition for the regeneration of hair split-ends that contains at least one mono- or di-saccharide (U.S. Pat. No. 4,900,545, assigned to Henkel); hair care compositions to improve hair strength, hold and volume that contain $C_5$ to $C_6$ carbohydrates such as glucose; the use of fucose in a hair treatment to prevent split ends (DE29709853, assigned to Goldwell GMBH); and the use of saccharides in a shampoo to improve combing properties and control hair damage (J09059134, assigned to Mikuchi Sangyo KK).

In essence, sugars have been applied to hair for countless reasons from moisturizing to enhancing hair growth (J10279439, assigned to Kureha Chem. Ind. Co. Ltd.). Clearly, however, not all sugars are the same and not all sugars impart the same properties when applied to a keratinous fiber.

The inventors have envisaged the application to at least one keratinous fiber of at least one composition comprising at least one compound chosen from $C_3$ to $C_5$ monosaccharides substituted with at least one $C_1$ to $C_{22}$ carbon chain. In particular, the inventors have discovered that compositions and methods using these compositions comprising applying to the at least one keratinous fiber at least one compound chosen from $C_3$ to $C_5$ monosaccharides substituted with at least one $C_1$ to $C_{22}$ carbon chain, and heating the at least one keratinous fiber are useful for durable non-permanent shaping of at least one keratinous fiber or for durable retention of a non-permanent shape of at least one keratinous fiber.

Thus, to achieve at least one of these and other advantages, the present invention, in one aspect, provides a composition for durable non-permanent shaping of at least one keratinous fiber or durable retention of a non-permanent shape of at least one keratinous fiber comprising at least one compound chosen from $C_3$ to $C_5$ monosaccharides substituted with at least one $C_1$ to $C_{22}$ carbon chain, and at least one film forming agent different from the at least one compound, wherein the at least one compound and the at least one film forming agent are present in an amount effective to impart a durable non-permanent shape to the at least one keratinous fiber or to durably retain a non-permanent shape of the at least one keratinous fiber. In one embodiment, the composition is heat-activated.

In another embodiment, the present invention is drawn to a method for durable non-permanent shaping of at least one keratinous fiber or durable retention of a non-permanent shape of at least one keratinous fiber comprising applying to the at least one keratinous fiber (i) at least one compound chosen from $C_3$ to $C_5$ monosaccharides substituted with at least one $C_1$ to $C_{22}$ carbon chain and (ii) at least one film forming agent different from the at least one compound; and heating the at least one keratinous fiber, wherein the at least one compound and at least one film forming agent are present in an amount effective to impart a durable non-permanent shape to the at least one at least one keratinous fiber or to durably retain a non-permanent shape of the at least one keratinous fiber, and further wherein the composition is applied prior to or during heating.

The present invention, in another aspect, provides a composition for durable non-permanent shaping of at least one keratinous fiber or durable retention of a non-permanent shape of at least one keratinous fiber comprising at least one compound chosen from $C_3$ to $C_5$ monosaccharides substituted with at least one $C_1$ to $C_{22}$ carbon chain, wherein the at least one compound is present in an amount effective to impart a durable non-permanent shape to the at least one keratinous fiber or to durably retain a non-permanent shape of the at least one keratinous fiber. In one embodiment, the composition is heat-activated.

In another embodiment, the present invention is drawn to a method for durable non-permanent shaping of at least one keratinous fiber or durable retention of a non-permanent shape of at least one keratinous fiber comprising applying to the at least one keratinous fiber at least one compound chosen from $C_3$ to $C_5$ monosaccharides substituted with at least one $C_1$ to $C_{22}$ carbon chain; and heating the at least one keratinous fiber, wherein the at least one compound is present in an amount effective to impart a durable non-permanent shape to the at least one at least one keratinous fiber or to durably retain a non-permanent shape of the at least one keratinous fiber, and further wherein the composition is applied prior to or during heating.

In yet another embodiment, the present invention provides a kit for durable non-permanent shaping of at least one keratinous fiber or durable retention of a non-permanent shape of at least one keratinous fiber comprising at least one compartment, wherein a first compartment comprises a first composition comprising at least one compound chosen from $C_3$ to $C_5$ monosaccharides substituted with at least one $C_1$ to $C_{22}$ carbon chain. In one embodiment, at least one compartment comprises at least one additional sugar, different from the at least one compound, and in another embodiment, at least one compartment comprises at least one film forming agent.

Certain terms used herein are defined below:

"At least one" as used herein means one or more and thus includes individual components as well as mixtures/combinations.

"Durable retention of a shape" as used herein means that, following at least six shampoos after treatment, treated hair still retains the ability to retain a particular shape after styling as compared to the ability of untreated hair to retain a particular shape after styling.

"Durable shaping," as used herein, refers to holding or keeping a shape of a keratinous fiber until the keratinous fiber is washed with water and/or shampoo. Retention of a shape can be evaluated by measuring, and comparing, the ability to retain a curl under conditions of high relative humidity of the treated hair and of the untreated hair in terms of Curl Efficiency (for example, see Examples 1 and 2).

"Heating" refers to the use of elevated temperature (i.e., above 100° C.). In one embodiment, the heating in the inventive method may be provided by directly contacting the at least one keratinous fiber with a heat source, e.g., by heat styling of the at least one keratinous fiber. Non-limiting examples of heat styling by direct contact with the at least one keratinous fiber include flat ironing, and curling methods using elevated temperatures (such as, for example, setting hair in curlers and heating, and curling with a curling iron and/or hot rollers). In another embodiment, the heating in the inventive method may be provided by heating the at least one keratinous fiber with a heat source which may not directly contact the at least one keratinous fiber. Non-limiting examples of heat sources which may not directly contact the at least one keratinous fiber include blow dryers, hood dryers, heating caps and steamers.

"A heat-activated" composition, as used herein, refers to a composition which, for example, shapes the at least one keratinous fiber better than the same composition which is not heated during or after application of the composition. Another example includes composition which retains a shape of at least one keratinous fiber better than the same composition which is not heated during or after application.

"High humidity" as defined herein refers to atmospheric humidity above 40%.

"Keratinous fibers" as defined herein may be human keratinous fibers, and may be chosen from, for example, hair.

"Non-permanent shaping" of keratinous fibers, as used herein, refers to a method of setting keratinous fibers in a particular shape or style which does not comprise breaking and reforming disulfide bonds within a keratinous fiber.

"Non-permanent shape" of keratinous fibers, as used herein, refers a shape or style of keratinous fibers obtained without breaking and reforming disulfide bonds within a keratinous fiber.

"Oligosaccharides" as defined herein refers to compounds generally comprising from two to ten monosaccharide units, which may be identical or different, bonded together.

"Polysaccharides" as defined herein refers to compounds generally comprising greater than ten monosaccharide units, which may be identical or different, bonded together.

"Polymers" as defined herein comprise copolymers (including terpolymers) and homopolymers.

It is to be understood that both the foregoing general description and the following detailed description are exemplary and explanatory only and are not restrictive of the invention, as claimed. Reference will now be made in detail to exemplary embodiments of the present invention.

As described above, sugars have been used in hair care compositions and other treatments for their moisture retaining properties. However, it was unexpectedly discovered by the present inventors that, in addition to retaining moisture, a certain class of sugars imparted a durable non-permanent shape or durable retention of a non-permanent shape or style to at least one keratinous fiber. In particular with respect to hair, compounds chosen from $C_3$ to $C_5$ monosaccharides substituted with at least one $C_1$ to $C_{22}$ carbon chain were found to impart good curl formation to the at least one keratinous fiber, and to prevent such curls from drooping, for example, due to humidity. Further, these compounds may impart to the at least one keratinous fiber an ability to retain a particular style even after shampooing the at least one keratinous fiber subsequent to treatment with a composition comprising at least one such compound. This is particularly true when the compounds are applied to the hair, and then the hair is heated.

Thus, the invention provides compositions for durable non-permanent shaping of at least one keratinous fiber or durable retention of a non-permanent shape of at least one keratinous fiber comprising (i) at least one compound chosen from $C_3$ to $C_5$ monosaccharides substituted with at least one $C_1$ to $C_{22}$ carbon chain and, optionally, (ii) at least one film forming agent, wherein the at least one compound and, optionally, the at least one film forming agent are present in an amount effective either to impart a durable non-permanent shape to the at least one keratinous fiber or to durably retain a non-permanent shape of the at least one keratinous fiber, depending on the embodiment. In one embodiment, the composition is heat-activated. In another embodiment, the composition both imparts a durable non-permanent shape to the at least one keratinous fiber and durably retains a non-permanent shape of the at least one keratinous fiber. The composition may further comprise at least one additional sugar.

The present invention also provides methods for durable non-permanent shaping of at least one keratinous fiber or for durable retention of a non-permanent shape of at least one keratinous fiber comprising applying to the at least one keratinous fiber a composition comprising (i) at least one compound chosen from $C_3$ to $C_5$ monosaccharides substituted with at least one $C_1$ to $C_{22}$ carbon chain and, optionally, (ii) at least one film forming agent; and heating the at least one keratinous fiber. The composition may be applied prior to or during heating. Further, the at least one compound and, optionally, the at least one film forming agent are present in an amount effective either to impart a durable non-permanent shape to the at least one keratinous fiber or to durably retain a non-permanent shape of the at least one keratinous fiber, depending on the embodiment. In one embodiment, the composition both imparts a durable non-permanent shape to the at least one keratinous fiber and durably retains a non-permanent shape of the at least one keratinous fiber. The composition may further comprise at least one additional sugar.

According to certain embodiments of the present invention, the at least one compound may be used in conjunction with at least one film-forming agent, such as, for example, film forming polymers and resins. For example, the film forming polymers may be chosen from cationic polymers, anionic polymers and nonionic polymers. Non-limiting examples of the at least one film forming agent are those listed at pages 1744 to 1747 of the CTFA International Cosmetic Ingredient Dictionary, $8^{th}$ edition (2000).

Abies Balsamea (Balsam Canada) Resin
Acrylamide/Ammonium Acrylate Copolymer
Acrylamides Copolymer
Acrylamides/DMAPA Acrylates/Methoxy PEG Methacrylate Copolymer
Acrylamide/Sodium Acrylate Copolymer
Acrylamidopropyltrimonium Chloride/Acrylamide Copolymer
Acrylamidopropyltrimonium Chloride/Acrylates Copolymer
Acrylates/Acetoacetoxyethyl Methacrylate Copolymer
Acrylates/Ammonium Methacrylate Copolymer
Acrylates Copolymer
Acrylates/Diacetoneacrylamide Copolymer
Acrylates/Dimethicone Copolymer
Acrylates/Dimethylaminoethyl Methacrylate Copolymer
Acrylates/Ethylhexyl Acrylate Copolymer
Acrylates/Hydroxyesters Acrylates Copolymer
Acrylates/Octylacrylamide Copolymer
Acrylates/PVP Copolymer
Acrylates/Stearyl Acrylate/Dimethicone Acrylate Copolymer
Acrylates/VA Copolymer
Acrylates/VA Crosspolymer
Acrylic Acid/Acrylonitrogens Copolymer
Adipic Acid/CHDM/MA/Neopentyl Glycol/Trimellitic Anhydride Copolymer
Adipic Acid/Diethylene Glycol/Glycerin Crosspolymer
Adipic Acid/Diethylenetriamine Copolymer
Adipic Acid/Dilinoleic Acid/Hexylene Glycol Copolymer
Adipic Acid/Dimethylaminohydoroxypropyl Diethylenetriamine Copolymer
Adipic Acid/Epoxypropyl Diethylenetriamine Copolymer
Adipic Acid/Fumaric Acid/Phthalic Acid/Tricyclodecane Dimethanol Copolymer
Adipic Acid/Isophthalic Acid/Neopentyl Glycol/Trimethylolpropane Copolymer
Adipic Acid/Neopentyl Glycol/Trimellitic Anhydride Copolymer
Albumen
Allyl Stearate/VA Copolymer
Aminoethylacrylate Phosphate/Acrylates Copolymer
Aminoethylpropanediol-Acrylates/Acrylamide Copolymer
Aminoethylpropanediol-AMPD-Acrylates/Diacetoneacrylamide Copolymer
Ammonium Acrylates/Acrylonitrogens Copolymer
Ammonium Acrylates Copolymer
Ammonium Alginate
Ammonium Polyacrylate
Ammonium Styrene/Acrylates Copolymer
Ammonium VA/Acrylates Copolymer
AMP-Acrylates/C1–18 Alkyl Acrylates/C1–8 Alkyl Acrylamide Copolymer
AMP-Acrylates Copolymer
AMP-Acrylates/Diacetoneacrylamide Copolymer
AMP-Acrylates/Dimethylaminoethylmethacrylate Copolymer
AMPD-Acrylates/Diacetoneacrylamide Copolymer
Astragalus Gummifer Gum
Avena Saliva (Oat) Kernel Protein
Benzoic Acid/Phthalic Anhydride/Pentaerythritol/Neopentyl Glycol/Palmitic Acid Copolymer
Brassica Campestris/Aleurites Fordi Oil Copolymer
Butadiene/Acrylonitrile Copolymer
Butoxy Chitosan
Butyl Acrylate/Ethylhexyl Methacrylate Copolymer
Butyl Acrylate/Hydroxyethyl Methacrylate Copolymer
Butyl Acrylate/Styrene Copolymer
Butylated Polyoxymethylene Urea
Butylated PVP
Butyl Benzoic Acid/Phthalic Anhydride/Trimethylolethane Copolymer
Butyl Ester of Ethylene/MA Copolymer
Butyl Ester of PVM/MA Copolymer
Calcium Carboxymethyl Cellulose
Calcium Carrageenan
Calcium/Sodium PVM/MA Copolymer
C1–5 Alkyl Galactomannan
Candelilla Wax Hydrocarbons
Carboxybutyl Chitosan
Carboxymethyl Chitosan
Carboxymethyl Chitosan Succinamide
Carboxymethyl Dextran Carboxymethyl Hydroxyethylcellulose
Castor Oil/IPDI Copolymer
Cellulose Acetate
Cellulose Acetate Butyrate
Cellulose Acetate Propionate
Cellulose Acetate Propionate Carboxylate
Cellulose Gum
Cetearyl Dimethicone/Vinyl Dimethicone Crosspolymer
Chitosan
Chitosan Adipate
Chitosan Ascorbate
Chitosan Formate
Chitosan Glycolate
Chitosan Lactate
Chitosan PCA
Chitosan Salicylate
Chitosan Succinamide
Collodion
Copaifera Officinalis (Balsam Copaiba) Resin
Copal
Corn Starch/Acrylamide/Sodium Acrylate Copolymer
Corn Starch/Modified
DEA-Styrene/Acrylates/DVB Copolymer
Dibutylhexyl IPDI
Didecyltetradecyl IPDI
Diethylene Glycolamine/Epichlorohydrin/Piperazine Copolymer
Diethylhexyl IPDI
Diglycol/CHDM/Isophthalates/SIP Copolymer
Diglycol/Isophthalates/SIP Copolymer
Dihydroxyethyl Tallowamine/IPDI Copolymer
Dilinoleic Acid/Glycol Copolymer
Dilinoleyl Alcohol/IPDI Copolymer
Dimethicone Copolyol/IPDI Copolymer
Dimethicone Copolyol Polyacrylate
Dimethicone/Sodium PG-Propyldimethicone Thiosulfate Copolymer
Dimethiconol/IPDI Copolymer
Dioctyldecyl IPDI
Dioctyldodecyl IPDI
Divinyldimethicone/Dimethicone Copolymer
Divinyldimethicone/Dimethicone Crosspolymer
DMAPA Acrylate/Acrylic Acid/Acrylonitrogens Copolymer
Dodecanedioic Acid/Cetearyl Alcohol/Glycol Copolymer
Ethylcellulose
Ethylene/Acrylic Acid Copolymer
Ethylene/Acrylic Acid/VA Copolymer
Ethylene/Calcium Acrylate Copolymer
Ethylene/MA Copolymer
Ethylene/Magnesium Acrylate Copolymer
Ethylene/Methacrytate Copolymer
Ethylene/Propylene Copolymer
Ethylene/Sodium Acrylate Copolymer
Ethylene/VA Copolymer
Ethylene/Zinc Acrylate Copolymer
Ethyl Ester of PVM/MA Copolymer
Euphorbia Cerifera (Candelilla) Wax
Flexible Collodion
Formaldehyde/Melamine/Tosylamide Copolymer
Galactoarabinan
Glycereth-7 Hydoxystearate/IPDI Copolymer
Glyceryl Polyacrylate
Glyceryl Polymethacrylate
Glycol Rosinate
Gutta Percha
Hexylene Glycol/Neopentyl Glycol/Adipic Acid/SMDI/ DMPA Copolymer
Hydrogenated Brassica Campestris/Aleurites Fordi Oil Copolymer
Hydrogenated Rosin
Hydrogenated Styrene/Butadiene Copolymer
Hydrolyzed Gadidae Protein
Hydrolyzed Wheat Protein
Hydrolyzed Wheat Protein/Dimethicone Copolyol Phosphate Copolymer
Hydrolyzed Wheat Protein/PVP Crosspolymer
Hydroxybutyl Methylcellulose
Hydroxyethylcellulose
Hydroxyethyl Chitosan
Hydroxyethyl Ethylcellulose
Hydroxyethyl/Methoxyethyl Acrylates Copolymer
Hydroxypropylcellulose
Hydroxypropyl Chitosan
Hydroxypropyl Guar
Hydroxypropyl Methylcellulose
Hydroxypropyl Methylcellulose Acetate/Succinate
Isobutylene/Ethylmaleimide Hydroxyethylmaleimide Copolymer
Isobutylene/MA Copolymer
Isobutylene/Sodium Maleate Copolymer
Isomerized Linoleic Acid
Isophorone Diamine/Isophthalic Acid/Trimethylolpropane Copolymer
Isopropyl Ester of PVM/MA Copolymer
Lauryl Acrylate/VA Copolymer
Lauryl Methacrylate/Glycol Dimethacrylate Copolymer
Maltodextrin
Mannan
Methacryloyl Ethyl Betaine/Acrylates Copolymer
Methoxypolyoxymethylene Melamine
Methyl Ethylcellulose
Methyl Methacrylate/Acrylonitrile Copolymer
Methyl Methacrylate Crosspolymer
Myrica Cerifera (Bayberry) Fruit Wax
Myroxylon Balsamum (Balsam Tolu) Resin
Myroxylon Pereirae (Balsam Peru) Resin
Nitrocellulose
Nylon-12/6/66 Copolymer
Octadecene/MA Copolymer
Octylacryamide/Acrylates/Butylaminoethyl Methacrylate Copolymer
Oxymethylene/Melamine Copolymer
PEG-150/Decyl Alcohol/SMDI Copolymer
PEG-150/Stearyl Alcohol/SMDI Copolymer
Perfluorononylethyl Stearyl Dimethicone
Phthalic Anhydride/Adipic Acid/Castor Oil/Neopentyl Glycol/PEG-3/Trimethylolpropane Copolymer
Phthalic Anhydride/Benzoic Acid/Glycerin Copolymer
Phthalic Anhydride/Benzoic Acid/Trimethylolpropane Copolymer
Phthalic Anhydride/Butyl Benzoic Acid/Propylene Glycol Copolymer
Phthalic Anhydride/Glycerin/Glycidyl Decanoate Copolymer
Piperylene/Butene/Pentene Copolymer
Polianthes Tuberosa Extract
Polyacrylamide
Polyacrylamidomethylpropane Sulfonic Acid
Polyacrylate-1
Polyacrytate-2
Polyacrylic Acid
Polybeta-Alanine
Polybeta-Alanine/Glutaric Acid Crosspolymer
Polybutyl Acrylate Polybutylene Terephthalate
Polychlorotrifluoroethylene
Polydiethyleneglycol Adipate/IPDI Copolymer
Polydimethylaminoethyl Methacrylate
Polyester-1
Polyethylacrylate
Polyethylene
Polyethylene Terephthalate
Polyethylglutamate
Polyethylmethacrylate
Polyglucuronic Acid
Polyglyceryl-2 Diisostearate/IPDI Copolymer
Polyisobutene
Polylysine
Polymethacrylamidopropyltrimonium Methosulfate
Polymethacrylic Acid
Polymethyl Acrylate
Polymethylglutamate
Polymethyl Methacrylate
Polyoxyisobutylene/Methylene Urea Copolymer
Polyoxymethylene Melamine
Polypentene
Polyperfluoraperhydrophenanthrene
Poly-p-Phenylene Terephthalamide
Polyquaternium-1
Polyquaternium-2
Polyquaternium-4
Polyquaternium-5
Polyquaternium-6
Polyquaternium-7
Polyquaternium-8
Polyquaternium-9
Polyquaternium-10
Polyquaternium-11
Polyquaternium-12
Polyquaternium-13
Polyquaternium-14
Polyquaternium-15
Polyquaternium-16
Polyquaternium-17
Polyquaternium-18
Polyquaternium-19
Polyquaternium-20
Polyquaternium-22
Polyquaternium-24
Polyquaternium-27
Polyquaternium-28
Polyquaternium-29
Polyquaternium-30
Polyquaternium-31
Polyquaternium-32
Polyquaternium-33
Polyquaternium-34
Polyquaternium-35
Polyquaternium-36
Polyquaternium-37
Polyquaternium-39
Polyquaternium-43
Polyquaternium-44
Polyquaternium-45
Polyquaternium-46
Polyquaternium-47
Polyquaternium-48
Polyquaternium-49
Polyquaternium-50
Polysilicone-6
Polysilicone-8
Polysilicone-11
Polystyrene
Polyurethane-1
Polyurethane-2
Polyurethane-4
Polyurethane-5
Polyvinyl Acetate
Polyvinyl Alcohol
Polyvinyl Butyral
Polyvinylcaprolactam
Polyvinyl Chloride
Polyvinyl Imidazolinium Acetate
Polyvinyl Laurate
Polyvinyl Methyl Ether
Polyvinyl Stearyl Ether
Potassium Carbomer
Potassium Carrageenan
PPG-26/HDI Copolymer
PPG-17/IPDI/DMPA Copolymer
PPG-12/SMDI Copolymer
PPG-7/Succinic Acid Copolymer
PPG-26/TDI Copolymer
Pseudotsuga Menziesii (Balsam Oregon) Resin
PVM/MA Copolymer
PVM/MA Decadiene Crosspolymer
PVP
PVP/Dimethlylaminoethylmethacrylate/Polycarbamyl
    Polyglycol Ester
PVP/Dimethlylaminoethylmethacrylate Copolymer
PVP/Dimethylaminoethylmethacrylate/Polycarbamyl
    Polyglycol Ester
PVP/Eicosene Copolymer
PVP/Hexadecene Copolymer
PVP Montmorillonite
PVP/Polycarbamyl Polyglycol Ester
PVP/VA Copolymer
PVP/VA/Itaconic Acid Copolymer
PVP/VA/Vinyl Propionate Copolymer
Quatermium-22
Rosin
Rubber Latex
Serum Albumin
Shellac
Sodium Acrylatevinyl Alcohol Copolymer
Sodium Acrylates Copolymer
Sodium Acrylates/Acrolein Copolymer
Sodium Acrylates/Acrylonitrogens Copolymer
Sodium Carbomer
Sodium Carboxymethyl Chitin
Sodium Carboxymethyl Starch
Sodium Carrageenan
Sodium C4–12Olefin/Maleic Acid Copolymer
Sodium DVB/Acrylates Copolymer
Sodium Isooctylene/MA Copolymer
Sodium MA/Diisobutylene Copolymer
Sodium MA/Vinyl Alcohol Copolymer
Sodium Polyacrylate
Sodium Polymethacrylate
Sodium Polystyrene Sulfonate
Sodium PVM/MA/Decadiene Crosspolymer
Sodium Styrene/Acrylates Copolymer
Sodium Tauride Acrylates/Acrylic Acid/Acrylonitrogens
    Copolymer
Starch/Acrylates/Acrylamide Copolymer
Starch Diethylaminoethyl Ether
Stearamidopropyl Dimethicone
Steareth-10 Allyl Ether/Acrylates Copolymer Stearylvinyl Ether/MA Copolymer
Styrax Benzoin Gum
Styrene/Acrylates/Acrylonitrile Copolymer
Styrene/Acrylates/Ammonium Methacrylate Copolymer
Styrene/Acrylates Copolymer
Styrene/Allyl Benzoate Copolymer
Styrene/DVB Copolymer
Styrene/Isoprene Copolymer
Styrene/MA Copolymer
Styrene/Methacrylamide/Acrylates Copolymer
Styrene/Methylstyrene/Indene Copolymer
Styrene/PVP Copolymer
Styrene/VA Copolymer
Sucrose Benzoate/Sucrose Acetate Isobutyrate/Butyl Benzyl Phthalate Copolymer
Sucrose Benzoate/Sucrose Acetate/Butyl Benzyl Phthalate/Methyl Methacrylates Copolymer
Sucrose Benzoate/Sucrose Acetate Isobutyrate Copolymer
TEA-Acrylates/Acrylonitrogens Copolymer
Terephthalic Acid/Isophthalic Acid/Sodium Isophthalic Acid Sulfonate/Glycol Copolymer
Tosylamide/Epoxy Resin
Tosylamide/Formaldehyde Resin
Tricontanyl PVP
Triethylene Glycol Rosinate
Trimethylolpropane Triacrylate
Trimethylpentanediol/Isophthalic Acid/Trimellitic Anhydride Copolymer
Triticum Vulgare (Wheat) Protein
Tromethamine Acrylates/Acrylonitrogens Copolymer
VA/Butyl Maleate/Isobornyl Acrylate Copolymer
VA/Crotonates Copolymer
VA/Crotonates/Methacryloxybenzophenone-1 Copolymer
VA/Crotonates/Vinyl Neodecanoate Copolymer
VA/Crotonates/Vinyl Propionate Copolymer
VA/Crotonic Acid/PEG-20M Copolymer
VA/DBM Copolymer
VA/Isobutyl Maleate/Vinyl Neodecanoate Copolymer
VA/Vinyl Butyl Benzoate/Crotonates Copolymer
Vinyl Acetate
Vinyl Caprolactam/PVP/Dimethylaminoethyl Methacrylate Copolymer
Yeast Betaglucan
Yeast Polysaccharides
Zein In one embodiment, the at least one film forming agent may be chosen from water soluble compounds, oil soluble compounds and compounds soluble in organic solvents. According to the present invention, the at least one film forming agent may be present in an amount generally ranging from 0.01% to 30% of active material by weight relative to the total weight of the composition, such as from 0.1% to 10% of active material by weight. One of ordinary skill in the art will recognize that the at least one film forming agent according to the present invention may be commercially available, and may come from suppliers in the form of a dilute solution. The amounts of the at least one film forming agent disclosed herein therefore reflect the weight percent of active material.

Other non-limiting examples of the at least one film forming agent include copolymers derived from (i) at least one vinyl monomer comprising at least one quaternary ammonium group and (ii) at least one additional monomer chosen from acrylamide, methacrylamide, alkyl acrylamides, dialkyl acrylamides, alkyl methacrylamides, dialkyl methacrylamides, alkyl acrylate, alkyl methacrylate, vinyl caprolactone, vinyl pyrrolidone, vinyl esters, vinyl alcohol, maleic anhydride, propylene glycol, and ethylene glycol.

Further non-limiting examples of the at least one film forming agent include:
vinyl acetate/vinyl tert butylbenzoate/crotonic acid terpolymers such as those described in U.S. Pat. No. 4,282,203, the disclosure of which is incorporated herein by reference;
N-octylacrylamide/methyl methacrylate/hydroxypropyl methacrylate/acrylic acid/tert-butylamino-ethyl methacrylate copolymers such as those sold by NATIONAL STARCH under the name "AMPHOMER LV-71";
corn starch/polyvinylpyrrolidone copolymers such as Corn Starch Modified sold by National Starch and Chemicals under the name Amaize®;
vinylpyrrolidone/vinyl acetate copolymers such as those sold by BASF under the name "LUVISKOL VA 64 Powder";
vinyl acetate/crotonic acid/vinyl neodecanoate terpolymers such as those sold by NATIONAL STARCH under the name "RESYN® 28-2930";
acrylic acid/ethyl acrylate/N-tert-butylacrylamide terpolymers such as those sold by BASF under the name "ULTRA-HOLD 8";
acrylic acid/acrylates/hydroxyacrylates/succinic acid copolymers such as Acrylates/C1–2 succinates hydroxyacrylates copolymer sold by ISP as ALLIANZ LT-120;
vinyl acetate/crotonic acid (90/10) copolymers such as those sold by BASF under the name "LUVISET CA 66";
acrylic acid/methacrylic acid/acrylates/methacrylates copolymers such as Acrylates Copolymer sold by Amerchol Corp. (Edison, N.J., USA); and
vinylcaprolactam/vinylpyrrolidone/dimethylamino ethyl methacrylate copolymers such as those sold by GAF under the name "POLYMER ACP-1018".

Further non-limiting examples of the at least one film forming agent include:
copolymers derived from (i) 1-vinyl-2-pyrrolidone and (ii) 1-vinyl-3-methylimidazolium salt (CTFA designation: polyquaternium-16), which is commercially available from BASF Corporation under the LUVIQUAT tradename (e.g., LUVIQUAT FC 370);
copolymers derived from reaction of (i) vinylcaprolactam and (ii) vinylpyrroldone with methylvinylimidazolium methosulfate, (CTFA designation: polyquaternium-46), which is commercially available from BASF;
copolymers derived from (i) vinylpyrrolidone and (ii) quaternized imidazoline monomers (CTFA designation: polyquaternium-44), which is commercially available from BASF;
copolymers derived from (i) 1-vinyl-2-pyrrolidone and (ii) 1-vinyl-3-methylimidazolium salt (CTFA designation: polyquaternium-16), which is commercially available from BASF Corporation under the LUVIQUAT tradename (e.g., LUVIQUAT FC 370);
poly(vinylamine), optionally quaternized;
poly-4-vinyl pyridine, optionally quaternized;
poly(ethyleneimine), optionally quaternized;
dimethyldiallylammonium chloride homopolymer (CTFA designation: polyquaternium-6);
copolymers derived from (i) acrylamide and (ii) dimethyldiallylammonium chloride (CTFA designation: polyquaternium-7);
copolymers derived from (i) dimethyldiallylammonium chloride and (ii) sodium acrylate (CTFA designation: Polyquaternium-22); and terpolymers derived from (i) dimethyldiallylammonium chloride, (ii) acrylic amide and (iii) sodium acrylate (CTFA designation: Polyquaternium-39).

Other non-limiting examples of the at least one film forming agent include derivatives of polysaccharide polymers such as cationic cellulose derivatives, for example, cationic cellulose, which is available from Amerchol Corp. (Edison, N.J., USA) in their Polymer JR™, LR™ and SR™ series of polymers, as salts of hydroxyethyl cellulose reacted with trimethyl ammonium substituted epoxide (CTFA designation: polyquaternium-10); polymeric quaternary ammonium salts of hydroxyethyl cellulose reacted with lauryl dimethyl ammonium-substituted epoxide (CTFA designation: polyquaternium-24), which is available from Amerchol Corp. (Edison, N.J., USA) under the tradename Polymer LM-200™; and cationic starch and derivatives thereof, such as quaternary starch, which is available from Croda.

In one embodiment, the at least one film forming agent is chosen from cationic polymers such as polyquaternium-16, polyquaternium-46, and polyquaternium-44. In another embodiment, the at least one film forming agent is chosen from nonionic polymers such as polymers derived from (1) corn starch and (2) polyvinylpyrrolidone; and copolymers derived from (1) vinyl acetate and (2) vinylpyrrolidone. In yet another embodiment, the at least one film forming agent is chosen from anionic polymers such as polymers derived from (1) vinyl acetate, (2) crotonic acid and (3) vinyl neodecanoate, polymers derived from (1) acrylic acid, (2) acrylates, (3) hydroxyacrylates and (4) succinic acid, and polymers derived from at least two monomers chosen from acrylic acid, methacrylic acid, esters of acrylic acid and esters of methacrylic acid. The at least one film forming agent chosen from anionic polymers can be neutralized in order to render the anionic polymers soluble.

The $C_3$ to $C_5$ monosaccharides according to the present invention may be chosen from any triose, tetrose and pentose. Further, the $C_3$ to $C_5$ monosaccharides can be chosen from the D-form, L-form and mixtures of any of the foregoing. Non-limiting examples of $C_3$ to $C_5$ monosaccharides include aldopentoses (such as xylose, arabinose, lyxose, and ribose), ketopentoses (such as ribulose and xylulose), aldotetroses (such as erythrose and treose), ketotetroses (such as erythrulose), aldotrioses (such as glyceraldehyde) and ketotrioses (such as dihydroxyacetone). The $C_3$ to $C_5$ monosaccharides may be chosen from $C_3$ to $C_5$ monosaccharides comprising aldehyde groups (aldoses), furanoses and other ring structures. The $C_3$ to $C_5$ monosaccharides may be further substituted with at least one group different from the $C_1$ to $C_{22}$ carbon chain.

Derivatives of $C_3$ to $C_5$ monosaccharides substituted with at least one $C_1$ to $C_{22}$ carbon chain may be used as the at least one compound of the present invention. For example, ammonias or primary amines may react with the aldehyde or ketone group of a sugar to form an imine derivative (i.e., a compound containing the functional group C=N). These imine compounds are sometimes also referred to as Schiff bases. Other non-limiting examples of derivatives of $C_3$ to $C_5$ monosaccharides are hemiacetal derivatives of $C_3$ to $C_5$ monosaccharides, hemiketal derivatives of $C_3$ to $C_5$ monosaccharides and any oxidized derivatives of $C_3$ to $C_5$ monosaccharides. These derivatives may be formed, for example, from the reaction of the aldehyde or ketone group of a sugar with an alcohol. Other exemplary derivatives of $C_3$ to $C_5$ monosaccharides may also include, but are not limited to, oligosaccharides derived from $C_3$ to $C_5$ monosaccharides, such as xylobiose. As previously mentioned, the at least one compound chosen from $C_3$ to $C_5$ monosaccharides substituted with at least one $C_1$ to $C_{22}$ carbon chain may be further substituted with at least one group different from the at least one $C_1$ to $C_{22}$ carbon chain. Thus, in one embodiment, the derivatives of $C_3$ to $C_5$ monosaccharides may be further substituted with at least one group different from the at least one $C_1$ to $C_{22}$ carbon chain.

According to the present invention, the at least one $C_1$ to $C_{22}$ carbon chain may be chosen from linear, branched and cyclic $C_1$ to $C_{22}$ carbon chains, which are saturated or unsaturated. The at least one $C_1$ to $C_{22}$ carbon chain may optionally be substituted. In one embodiment, the at least one $C_1$ to $C_{22}$ carbon chain is chosen from $C_{16}$ to $C_{18}$ carbon chains. In another embodiment, the at least one $C_1$ to $C_{22}$ carbon chain is chosen from $C_{16}$ carbon chains and $C_{18}$ carbon chains. Non-limiting examples of $C_{16}$ carbon chains are linear hexadecyl chains, and non-limiting examples of $C_{18}$ carbon chains are linear octadecyl chains.

Further, the $C_3$ to $C_5$ monosaccharides may be substituted with the at least one $C_1$ to $C_{22}$ carbon chain at any position on the sugar. For example, in one embodiment, a $C_3$ to $C_5$ monosaccharide is substituted with at least one $C_1$ to $C_{22}$ carbon chain at the C1 position of the $C_3$ to $C_5$ monosaccharide. In another embodiment, a $C_3$ to $C_5$ monosaccharide is substituted with the at least one $C_1$ to $C_{22}$ carbon chain at at least one of the hydroxyl groups of the $C_3$ to $C_5$ monosaccharide. As used herein, substituted at at least one of the hydroxyl groups of a $C_3$ to $C_5$ monosaccharide means at least one of substitution on the hydroxyl group itself (i.e., formation of an ether linkage between the $C_3$ to $C_5$ monosaccharide and the $C_1$ to $C_{22}$ carbon chain) and substitution on the carbon atom to which the hydroxyl group is commonly bonded. Further, the $C_3$ to $C_5$ monosaccharides may be substituted with the at least one $C_1$ to $C_{22}$ carbon chain at a carbon atom bearing no hydroxyl groups (i.e., a $CH_2$ within the $C_3$ to $C_5$ monosaccharide or a carbon atom within the $C_3$ to $C_5$ monosaccharide bearing substituents other than a hydroxyl group). Further, the $C_3$ to $C_5$ monosaccharides may be further substituted with at least one substituent different from the at least one $C_1$ to $C_{22}$ carbon chain.

According to the present invention, the at least one compound chosen from $C_3$ to $C_5$ monosaccharides substituted with at least one $C_1$ to $C_{22}$ carbon chain is present in the composition in an amount generally ranging from 0.01% to 10% by weight relative to the total weight of the composition, such as from 0.1% to 5% by weight.

The compositions of the present invention as well as those of the inventive methods may further comprise at least one additional sugar which is different from the at least one compound chosen from $C_3$ to $C_5$ monosaccharides substituted with at least one $C_1$ to $C_{22}$ carbon chain. The at least one additional sugar may, for example, aid in moisture retention. The effectiveness of a sugar in aiding in moisture retention may be measured by monitoring a DSC peak at a temperature ranging from 75° C. to 200° C.

The at least one additional sugar may be chosen from any sugar, carbohydrate and carbohydrate moiety. Non-limiting examples of the at least one additional sugar are monosaccharides, which include, but are not limited to, three to seven carbon sugars such as pentoses (for example, ribose, arabinose, xylose, lyxose, ribulose, and xylulose) and hexoses (for example, allose, altrose, glucose, mannose, gulose, idose, galactose, talose, sorbose, psicose, fructose, and tagatose); oligosaccharides such as disaccharides (such as maltose, sucrose, cellobiose, trehalose and lactose); and polysaccharides such as starch, dextrins, cellulose and glycogen. In one embodiment, the at least one additional sugar of the invention are chosen from any aldoses and ketoses.

Further, the at least one additional sugar may be substituted or unsubstituted. For example, the at least one additional sugar may be substituted with at least one $C_1$ to $C_{22}$ carbon chain. In one embodiment, the at least one $C_1$ to $C_{22}$ carbon chain is chosen from linear, branched and cyclic $C_1$ to $C_{22}$ carbon chains, which are saturated or unsaturated. For example, the at least one $C_1$ to $C_{22}$ carbon chain may be chosen from $C_{16}$ to $C_{18}$ carbon chains (such as $C_{16}$ carbon chains and $C_{18}$ carbon chains). Further, for example, $C_{16}$ carbon chains may be chosen from linear hexadecyl chains and $C_{18}$ carbon chains may be chosen from linear octadecyl chains. In one embodiment, the at least one additional sugar is substituted with at least one $C_1$ to $C_{22}$ carbon chain at the C1 position of the at least additional one sugar.

According to the present invention, the at least one additional sugar is present in the composition in an amount generally ranging from 0.01% to 10% by weight relative to the total weight of the composition, such as from 0.1% to 5% by weight.

The compositions of the present invention as well as those of the inventive methods may be in the form of a liquid, an oil, a paste, a stick, a dispersion, an emulsion, a lotion, a gel, or a cream. Further, these compositions may further comprise at least one suitable additive chosen from additives commonly used in compositions for keratinous fibers. Non-limiting examples of the at least one suitable additive include anionic surfactants, cationic surfactants, nonionic surfactants, amphoteric surfactants, fragrances, penetrating agents, antioxidants, sequestering agents, opacifying agents, solubilizing agents, emollients, colorants, screening agents (such as sunscreens and UV filters), preserving agents, proteins, vitamins, silicones, polymers such as thickening polymers, plant oils, mineral oils, synthetic oils and any other additive conventionally used in compositions for the care and/or treatment of keratinous fibers.

Needless to say, a person skilled in the art will take care to select the at least one suitable additive such that the advantageous properties of the composition in accordance with the invention are not, or are not substantially, adversely affected by the addition(s) envisaged.

The compositions of the present invention and those used in the methods of the present invention may also be provided as one-part compositions comprising at least one compound chosen from $C_3$ to $C_5$ monosaccharides substituted with at least one $C_1$ to $C_{22}$ carbon chain and, optionally, at least one additional sugar, and further, optionally at least one film forming agent, or in the form of a multi-component treatment or kit. The skilled artisan, based on the stability of the composition and the application envisaged, will be able to determine how the composition and/or multicomponent compositions should be stored and mixed. For example, simple sugars such as $C_3$ to $C_5$ monosaccharides are known to be stable at pH levels ranging from 4 to 9. In compositions where the pH range is below or above these levels, the sugars would be stored separately and added to the composition only at the time of application.

Thus, the present invention also relates to a kit for durable non-permanent shaping of at least one keratinous fiber or for durable retention of a non-permanent shape of at least one keratinous fiber comprising at least one compartment, wherein a first compartment comprises a first composition comprising at least one compound chosen from $C_3$ to $C_5$ monosaccharides substituted with at least one $C_1$ to $C_{22}$ carbon chain. In one embodiment, the first composition further comprises at least one additional sugar, different from the at least one compound, while in another embodiment, the first composition further comprises at least one film forming agent.

According to one aspect of the invention, the at least one compound suitable for the present invention is a mixture of pentoses substituted with at least one $C_1$ to $C_{22}$ carbon chain. XYLIANCE brand modified pentoses is a blend of hexadecyl glycosides and octadecyl glycosides wherein the glycosides comprise D-xylosides, L-arabinosides, and D-glucosides. XYLIANCE may be obtained from Soliance, Route de Bazancourt-51110 Pomacle, France.

Unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should be construed in light of the number of significant digits and ordinary rounding approaches.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements. The following examples are intended to illustrate the invention without limiting the scope as a result.

EXAMPLES 1 AND 2

Unless otherwise noted, the following procedure was used in the following examples to determine the efficiency of $C_3$ to $C_5$ monosaccharides substituted with at least one $C_1$ to $C_{22}$ carbon chain. Hair swatches (2 g., 6.5–7.5 in.) were treated with a solution of film former/XYLIANCE (0.5 g solution/g of hair) then blow dried. The hair swatches were then styled with a curling iron for 1 minute and the curly swatches were placed in a humidity chamber at 90% relative humidity for 1 hour.

The Curl Efficiency was calculated as:

$$L_t/L_o \times 100$$

Where:

$L_o$ represents the original length of fully extended hair $L_t$ represents the length of the hair after 1 hour in the humidity chamber A lower Curl Efficiency represents a better curl retention.

EXAMPLE 1

Curl Efficiency of XYLIANCE and Film Former

Hair was treated as described above with styling solutions that contain 3% of Octylacrylamide/Acrylates/Butylaminoethyl/Methacrylate Copolymer (AMPHOMER LV-71 from National Starch and Chemicals Co.), and varying amounts of XYLIANCE. The results are shown in Table 10.

TABLE 1

Curl Efficiency of Hair Treated with Amphomer LV-71 and XYLIANCE

| Styling Solution | Curl Efficiency |
|---|---|
| 3% Amphomer LV-71/0% XYLIANCE | 76 |
| 3% Amphomer LV-71/0.1% XYLIANCE | 72 |
| 3% Amphomer LV-71/0.5% XYLIANCE | 61 |
| 3% Amphomer LV-71/1% XYLIANCE | 60 |

The data indicates that XYLIANCE improved the curl efficiency of hair that was treated with styling polymer.

EXAMPLE 2
Effects of Xyliance and Neutralized Film Former

Hair was treated as described above with solutions of 0.5% XYLIANCE and 6% Amphomer LV-71 that had been neutralized with AMP at various degrees of neutralization. The results are shown in Table 11.

TABLE 2

Curl Efficiency of Hair Treated with 0.5% XYLIANCE and 6% Amphomer LV-71 with Various Degrees of Neutralization

| Degree of Neutralization | Curl Efficiency |
|---|---|
| 0% Neutralization/0% XYLIANCE | 84 |
| 0% Neutralization/0.5% XYLIANCE | 73 |
| 40% Neutralization/0% XYLIANCE | 67 |
| 40% Neutralization/0.5% XYLIANCE | 57 |
| 80% Neutralization/0% XYLIANCE | 63 |
| 80% Neutralization/0.5% XYLIANCE | 59 |
| 100% Neutralization/0% XYLIANCE | 59 |
| 100% Neutralization/0.5% XYLIANCE | 56 |

The data indicate that XYLIANCE improved the curl retention of hair that was heat treated with styling polymer with various degrees of neutralization.

EXAMPLE 3

The following procedure was used to treat the hair and measure the Curl Droop: Hair swatches (2 g., 6.5–7.5 in.) were treated with an ethanol solution containing 6% Resyn® 28-2930 (neutralized to 85% with AMP) and 1% Xyliance (0.5 g solution/g of hair) then blow dried. The hair swatches were then heated with a flat iron for 1 minute and then shampooed with 10% sodium laureth sulfate (SLES). The treatment was repeated up to 6 times, as indicated. The treated hair swatches were shampooed 2, 4, and 6 times, then styled with a curling iron for 30 seconds and placed in a humidity chamber at 90% relative humidity to measure the Curl Droop. As the curl slowly relaxed in the humidity chamber, the length of the hair swatches was measured every minute (up to 15 minutes).

The Curl Droop was calculated as:

$$[(L_o-L_t)/(L_o-L_i)] \times 100$$

Where:

$L_o$ represents the original length of fully extended hair $L_t$ represents the length of the hair at time t in the humidity chamber $L_i$ represents the initial length of the hair at time 0 in the humidity chamber (i.e., after styling with a curling iron for 30 seconds)

A higher Curl Droop represents a better curl retention.

TABLE 1

Curl Droop of Hair Treated with Corn Starch Modified

| Solution Comprising 6% (active) Resyn ® 28-2930 (85% neutralized) | 0 minutes | 5 minutes | 10 minutes | 15 minutes |
|---|---|---|---|---|
| Without Xyliance, after treatment | 100 | 94 | 86 | 75 |
| With Xyliance, after treatment | 100 | 95 | 89 | 77 |
| Without Xyliance, after 2 shampoos | 100 | 91 | 83 | 71 |
| With glucosamine, after 2 shampoos | 100 | 93 | 86 | 72 |
| Without glucosamine, after 4 shampoos | 100 | 90 | 75 | 57 |
| With glucosamine, after 4 shampoos | 100 | 91 | 78 | 65 |
| Without glucosamine, after 6 shampoos | 100 | 59 | 45 | 27 |
| With glucosamine, after 6 shampoos | 100 | 88 | 75 | 57 |

The data showed that hair treated with at least one film forming agent (Resyn® 28-2930 (neutralized to 85% with AMP)), at least one compound chosen from $C_3$ to $C_5$ monosaccharides substituted with at least one $C_1$ to $C_{22}$ carbon chain (Xyliance) and heat had a higher curl retention than hair treated with at least one film forming agent (Resyn® 28-2930 (neutralized to 85% with AMP)) and heat but without at least one compound chosen from $C_3$ to $C_5$ monosaccharides substituted with at least one $C_1$ to $C_{22}$ carbon chain even after 6 shampoos.

What is claimed is:

1. A composition for durable non-permanent shaping or durable retention of a non-permenent shape of least one keratinous fiber comprising:
    (a) at least one film forming agent; and
    (b) at least one compound chosen from $C_3$ to $C_5$ monosaccharides substituted with at least one $C_1$ to $C_{22}$ carbon chain,
    wherein said at least one film forming agent and said at least one compound are present in an amount effective to impart a durable non-permanent shape to said at least one keratinous fiber or to durably retain a non-permanent shape of said at least one keratinous fiber, and
    wherein said $C_3$ to $C_5$ monosaccharides are chosen from tetroses.

2. A composition according to claim 1, wherein said tetroses are chosen from aldotetroses and ketotetroses.

3. A composition according to claim 2, wherein said aldotetroses are chosen from erythrose and treose.

4. A composition according to claim 2, wherein said tetroses are erythrulose.

5. A composition for durable non-permanent shaping or durable retention of a non-permanent shape of least one keratinous fiber comprising:
    (a) at least one film forming agent; and
    (b) at leasat one compound chosen from $C_3$ to $C_5$ monosaccharides substituted with at least one $C_1$ to $C_{22}$ carbon chain,
    wherein said at least one film forming agent and said at least one compound are present in an amount effective to impart a durable non-permanent shape to said at least one keratinous fiber or to durably retain a non-permanent shape of said at least one keratinous fiber, and
    wherein said $C_3$ to $C_5$ monosaccharides are chosen from trioses.

6. A composition according to claim 5, wherein said trioses are chosen from aldotrioses and ketotrioses.

7. A composition according to claim 6, wherein said trioses are glyceraldehyde.

8. A composition according to claim 6, wherein said trioses are dihydroxyacetone.

9. A method for durable non-permanent shaping of at least one keratinous fiber or for durable retention of a non-permanent shape of at least one keratinous fiber comprising:
applying to said at least one keratinous fiber a composition comprising:
(a) at least one film forming agent, and
(b) at least one compound chosen from $C_3$ to $C_5$ monosaccharides substituted with at least one $C_1$ to $C_{22}$ carbon chain; and
heating said at least one keratinous fiber,
wherein said at least one film forming agent and said at least one compound are present in an amount effective to impart a durable non-permanent shape to said at least one keratinous fiber or to durably retain a non-permanent shape of said at least one keratinous fiber, and
further wherein said composition is applied prior to said heating or during said heating.

10. A method according to claim 9, further comprising wetting said at least one keratinous fiber with water prior to said application.

11. A method according to claim 9, further comprising shampooing said at least one keratinous fiber subsequent to said heating.

12. A method according to claim 11, further comprising rinsing said at least one keratinous fiber subsequent to said shampooing.

13. A method according to claim 9, wherein said at least one film forming agent is chosen from film forming polymers and film forming resins.

14. A method according to claim 13, wherein said film forming polymers are chosen from cationic polymers.

15. A method according to claim 14, wherein said cationic polymers are chosen from polyquaternium-16, polyquaternium-46 and polyquaternium-44.

16. A method according to claim 13, wherein said film forming polymers are chosen from nonionic polymers.

17. A method according to claim 16, wherein said nonionic polymers are chosen from:
(i) polymers derived from (1) corn starch and (2) polyvinylpyrrolidone; and
(ii) copolymers derived from (1) vinyl acetate and (2) vinylpyrrolidone.

18. A method according to claim 13, wherein said film forming polymers are chosen from anionic polymers.

19. A method according to claim 18, wherein said anionic polymers are chosen from:
(i) polymers derived from (1) vinyl acetate, (2) crotonic acid and (3) vinyl neodecanoate;
(ii) polymers derived from (1) acrylic acid, (2) acrylates, (3) hydroxyacrylates and (4) succinic acid; and
(iii) polymers derived from at least two monomers chosen from acrylic acid, methacrylic acid, esters of acrylic acid, and esters of methacrylic acid.

20. A method according to claim 18, wherein said anionic polymers are neutralized.

21. A method according to claim 9, wherein said at least one film forming agent is present in said composition in an amount ranging from 0.01% to 30% by weight relative to the total weight of the composition.

22. A method according to claim 21, wherein said at least one film forming agent is present in said composition in an amount ranging from 0.1% to 10% by weight relative to the total weight of the composition.

23. A method according to claim 9, wherein said $C_3$ to $C_5$ monosaccharides are chosen from pentoses.

24. A method according to claim 23, wherein said pentoses are chosen from aldopentoses and ketopentoses.

25. A method according to claim 24, wherein said aldopentoses are chosen from xylose, arabinose, lyxose, and ribose.

26. A method according to claim 24, wherein said ketopentoses are chosen from ribulose and xylulose.

27. A method according to claim 9, wherein said $C_3$ to $C_5$ monosaccharides are chosen from tetroses.

28. A method according to claim 27, wherein said tetroses are chosen from aldotetroses and ketotetroses.

29. A method according to claim 28, wherein said aldotetroses are chosen from erythrose and treose.

30. A method according to claim 28, wherein said tetroses are erythrulose.

31. A method according to claim 9, wherein said $C_3$ to $C_5$ monosaccharides are chosen from trioses.

32. A method according to claim 31, wherein said trioses are chosen from aldotrioses and ketotrioses.

33. A method according to claim 32, wherein said trioses are glyceraldehyde.

34. A method according to claim 32, wherein said trioses are dihydroxyacetone.

35. A method according to claim 9, wherein said $C_3$ to $C_5$ monosaccharides are chosen from furanoses and derivatives thereof.

36. A method according to claim 9, wherein said $C_3$ to $C_5$ monosaccharides are chosen from derivatives of $C_3$ to $C_5$ monosaccharides.

37. A method according to claim 36, wherein said derivatives of $C_3$ to $C_5$ monosaccharides are chosen from imine derivatives of $C_3$ to $C_5$ monosaccharides, hemiacetal derivatives of $C_3$ to $C_5$ monosaccharides, hemiketal derivatives of $C_3$ to $C_5$ monosaccharides, and oxidized derivatives of $C_3$ to $C_5$ monosaccharides.

38. A method according to claim 36, wherein said derivatives of $C_3$ to $C_5$ monosaccharides are further substituted with at least one group different from said at least one $C_1$ to $C_{22}$ carbon chain.

39. A method according to claim 9, wherein said at least one $C_1$ to $C_{22}$ carbon chain is chosen from linear, branched and cyclic $C_1$ to $C_{22}$ carbon chains, which are saturated or unsaturated.

40. A method according to claim 9, wherein said at least one $C_3$ to $C_5$ carbon chain is substituted.

41. A method according to claim 9, wherein said at least one $C_1$ to $C_{22}$ carbon chain is chosen from $C_{16}$ to $C_{18}$ carbon chains.

42. A method according to claim 9, wherein said at least one $C_1$ to $C_{22}$ carbon chain is chosen from $C_{16}$ carbon chains and $C_{18}$ carbon chains.

43. A method according to claim 42, wherein said $C_{16}$ carbon chains are linear hexadecyl chains.

44. A method according to claim 42, wherein said $C_{18}$ carbon chains are linear octadecyl chains.

45. A method according to claim 9, wherein said at least one compound is substituted with said at least one $C_1$ to $C_{22}$ carbon chain at a $CH_2$ position of said $C_3$–$C_5$ monosaccharides.

46. A method according to claim 9, wherein said at least one compound is substituted with said at least one $C_1$ to $C_{22}$ carbon chain at at least one of the hydroxyl groups of said $C_3$–$C_5$ monosaccharide.

47. A method according to claim 9, wherein said at least one compound is present in said composition in an amount ranging from 0.01% to 10% by weight relative to the total weight of the composition.

48. A method according to claim 9, wherein said at least one compound is present in said composition in an amount ranging from 0.1% to 5% by weight relative to the total weight of the composition.

49. A method according to claim 9, wherein said composition further comprises at least one additional sugar different from said at least one compound chosen from $C_3$ to $C_5$ monosaccharides substituted with at least one $C_1$ to $C_{22}$ carbon chain.

50. A method according to claim 49, wherein said at least one additional sugar is chosen from monosaccharides, oligosaccharides and polysaccharides.

51. A method according to claim 50, wherein said monosaccharides are chosen from hexoses.

52. A method according to claim 51, wherein said hexoses are chosen from allose, altrose, glucose, mannose, gulose, idose, galactose, talose, sorbose, psicose, fructose, and tagatose.

53. A method according to claim 50, wherein said at least one additional sugar is substituted with at least one $C_1$ to $C_{22}$ carbon chain.

54. A method according to claim 53, wherein said at least one $C_1$ to $C_{22}$ carbon chain is chosen from linear, branched and cyclic $C_1$ to $C_{22}$ carbon chains, which are saturated or unsaturated.

55. A method according to claim 54, wherein said at least one $C_1$ to $C_{22}$ carbon chain is chosen from $C_{16}$ to $C_{18}$ carbon chains.

56. A method according to claim 54, wherein said at least one $C_1$ to $C_{22}$ carbon chain is chosen from $C_{16}$ carbon chains and $C_{18}$ carbon chains.

57. A method according to claim 56, wherein said $C_{16}$ carbon chains are linear hexadecyl chains.

58. A method according to claim 56, wherein said $C_{18}$ carbon chains are linear octadecyl chains.

59. A method according to claim 53, wherein said at least one additional sugar is substituted with said at least one $C_1$ to $C_{22}$ carbon chain at the $C_1$ position of said at least one additional sugar.

60. A method according to claim 53, wherein said at least one additional sugar is present in said composition in an amount ranging from 0.01% to 10% by weight relative to the total weight of the composition.

61. A method according to claim 60, wherein said at least one additional sugar is present in said composition in an amount ranging from 0.1% to 5% by weight relative to the total weight of the composition.

62. A method according to claim 9, wherein said composition is in the form of a liquid, oil, paste, stick, dispersion, emulsion, lotion, gel, or cream.

63. A method according to claim 9, wherein said at least one keratinous fiber is hair.

64. A method according to claim 9, further comprising at least one suitable additive chosen from anionic surfactants, cationic surfactants, nonionic surfactants, amphoteric surfactants, fragrances, penetrating agents, antioxidants, sequestering agents, opacifying agents, solubilizing agents, emollients, colorants, screening agents, preserving agents, proteins, vitamins, silicones, polymers such as thickening polymers, plant oils, mineral oils, and synthetic oils.

65. A method according to claim 9, wherein said composition is applied prior to and during said heating.

66. A method for durable non-permanent shaping of at least one keratinous fiber or for durable retention of a non-permanent shape of at least one keratinous fiber comprising:

applying to said at least one keratinous fiber a composition comprising at least one compound chosen from $C_3$ to $C_5$ monosaccharides substituted with at least one $C_1$ to $C_{22}$ carbon chain; and heating said at least one keratinous fiber, wherein said at least one compound is present in an amount effective to impart a durable non-permanent shape to said at least one keratinous fiber or to durably retain a non-permanent shape of said at least one keratinous fiber, and further wherein said composition is applied prior to said heating or during said heating.

67. A method according to claim 66, further comprising wetting said at least one keratinous fiber with water prior to said applying.

68. A method according to claim 66, further comprising shampooing said at least one keratinous fiber subsequent to said heating.

69. A method according to claim 68, further comprising rinsing said at least one keratinous fiber subsequent to said shampooing.

70. A method according to claim 66, wherein said $C_3$ to $C_5$ monosaccharides are chosen from pentoses.

71. A method according to claim 70, wherein said pentoses are chosen from aldopentoses and ketopentoses.

72. A method according to claim 71, wherein said aldopentoses are chosen from xylose, arabinose, lyxose, and ribose.

73. A method according to claim 71, wherein said ketopentoses are chosen from ribulose and xylulose.

74. A method according to claim 66, wherein said $C_3$ to $C_5$ monosaccharides are chosen from tetroses.

75. A method according to claim 74, wherein said tetroses are chosen from aldotetroses and ketotetroses.

76. A method according to claim 75, wherein said aldotetroses are chosen from erythrose and treose.

77. A method according to claim 75, wherein said tetroses are erythrulose.

78. A method according to claim 66, wherein said $C_3$ to $C_5$ monosaccharides are chosen from trioses.

79. A method according to claim 78, wherein said trioses are chosen from aldotrioses and ketotrioses.

80. A method according to claim 79, wherein said trioses are glyceraldehyde.

81. A method according to claim 79, wherein said trioses are dihydroxyacetone.

82. A method according to claim 66, wherein said $C_3$ to $C_5$ monosaccharides are chosen from furanoses and derivatives thereof.

83. A method according to claim 66, wherein said $C_3$ to $C_5$ monosaccharides are chosen from derivatives of $C_3$ to $C_5$ monosaccharides.

84. A method according to claim 83, wherein said derivatives of $C_3$ to $C_5$ monosaccharides are chosen from imine derivatives of $C_3$ to $C_5$ monosaccharides, hemiacetal derivatives of $C_3$ to $C_5$ monosaccharides, hemiketal derivatives of $C_3$ to $C_5$ monosaccharides, and oxidized derivatives of $C_3$ to $C_5$ monosaccharides.

85. A method according to claim 83, wherein said derivatives of $C_3$ to $C_5$ monosaccharides are further substituted with at least one group different from said at least one $C_1$ to $C_{22}$ carbon chain.

86. A method according to claim 66, wherein said at least one $C_1$ to $C_{22}$ carbon chain is chosen from linear, branched and cyclic $C_1$ to $C_{22}$ carbon chains, which are saturated or unsaturated.

87. A method according to claim 66, wherein said at least one $C_1$ to $C_{22}$ carbon chain is substituted.

88. A method according to claim 66, wherein said at least one $C_1$ to $C_{22}$ carbon chain is chosen from $C_{16}$ to $C_{18}$ carbon chains.

89. A method according to claim 66, wherein said at least one $C_1$ to $C_{22}$ carbon chain is chosen from $C_{16}$ carbon chains and $C_{18}$ carbon chains.

90. A method according to claim 89, wherein said $C_{16}$ carbon chains are linear hexadecyl chains.

91. A method according to claim 89, wherein said $C_{18}$ carbon chains are linear octadecyl chains.

92. A method according to claim 66, wherein said at least one compound is substituted with said at least one $C_1$ to $C_{22}$ carbon chain at a $CH_2$ position of said $C_3$–$C_5$ monosaccharides.

93. A method according to claim 66, wherein said at least one compound is substituted with said at least one $C_1$ to $C_{22}$ carbon chain at at least one of the hydroxyl groups of said $C_3$–$C_5$ monosaccharide.

94. A method according to claim 66, wherein said at least one compound is present in said composition in an amount ranging from 0.01% to 10% by weight relative to the total weight of the composition.

95. A method according to claim 94, wherein said at least one compound is present in said composition in an amount ranging from 0.1% to 5% by weight relative to the total weight of the composition.

96. A method according to claim 66, wherein said composition further comprises at least one additional sugar different from said at least one compound chosen from $C_3$ to $C_5$ monosaccharides substituted with at least one $C_1$ to $C_{22}$ carbon chain.

97. A method according to claim 96, wherein said at least one additional sugar is chosen from monosaccharides, oligosaccharides and polysaccharides.

98. A method according to claim 97, wherein said monosaccharides are chosen from hexoses.

99. A method according to claim 98, wherein said hexoses are chosen from allose, altrose, glucose, mannose, gulose, idose, galactose, talose, sorbose, psicose, fructose, and tagatose.

100. A method according to claim 96, wherein said at least one additional sugar is substituted with at least one $C_1$ to $C_{22}$ carbon chain.

101. A method according to claim 100, wherein said at least one $C_1$ to $C_{22}$ carbon chain is chosen from linear, branched and cyclic $C_1$ to $C_{22}$ carbon chains, which are saturated or unsaturated.

102. A method according to claim 101, wherein said at least one $C_1$ to $C_{22}$ carbon chain is chosen from $C_{16}$ to $C_{18}$ carbon chains.

103. A method according to claim 101, wherein said at least one $C_1$ to $C_{22}$ carbon chain is chosen from $C_{16}$ carbon chains and $C_{18}$ carbon chains.

104. A method according to claim 103, wherein said $C_{16}$ carbon chains are linear hexadecyl chains.

105. A method according to claim 103, wherein said $C_{18}$ carbon chains are linear octadecyl chains.

106. A method according to claim 100, wherein said at least one additional sugar is substituted with said at least one $C_1$ to $C_{22}$ carbon chain at the $C_1$ position of said at least one additional sugar.

107. A method according to claim 96, wherein said at least one additional sugar is present in said composition in an amount ranging from 0.01% to 10% by weight relative to the total weight of the composition.

108. A method according to claim 101, wherein said at least one additional sugar is present in said composition in an amount ranging from 0.1% to 5% by weight relative to the total weight of the composition.

109. A method according to claim 66, wherein said composition is in the form of a liquid, oil, paste, stick, dispersion, emulsion, lotion, gel, or cream.

110. A method according to claim 66, wherein said at least one keratinous fiber is hair.

111. A method according to claim 66, further comprising at least one suitable additive chosen from anionic surfactants, cationic surfactants, nonionic surfactants, amphoteric surfactants, fragrances, penetrating agents, antioxidants, sequestering agents, opacifying agents, solubilizing agents, emollients, colorants, screening agents, preserving agents, proteins, vitamins, silicones, polymers such as thickening polymers, plant oils, mineral oils, and synthetic oils.

112. A method according to claim 66, wherein said composition is applied prior to and during said heating.

* * * * *

UNITED STATES PATENT AND TRADEMARK OFFICE
CERTIFICATE OF CORRECTION

PATENT NO.        : 6,800,302 B2
APPLICATION NO. : 09/820856
DATED             : October 5, 2004
INVENTOR(S)       : David W. Cannell et al.

Page 1 of 1

It is certified that error appears in the above-identified patent and that said Letters Patent is hereby corrected as shown below:

In claim 1, column 18, line 34, "of least" should read --of at least--.

In claim 5, column 18, line 54, "of least" should read --of at least--.

In claim 5, column 18, line 57, "leasat" should read --least--.

In claim 48, column 21, line 5, "claim 9," should read --claim 47,--.

In claim 108, column 24, line 22, "claim 101," should read --claim 107,--.

Signed and Sealed this

Twenty-first Day of April, 2009

JOHN DOLL
*Acting Director of the United States Patent and Trademark Office*